United States Patent [19]

Vales

[11] Patent Number: 5,228,345
[45] Date of Patent: Jul. 20, 1993

[54] APPARATUS FOR COLLECTING SAMPLES FROM GROUND-HOLES

[75] Inventor: Enoch S. Vales, Waterloo, Canada
[73] Assignee: University of Waterloo, Waterloo, Canada
[21] Appl. No.: 607,029
[22] Filed: Oct. 31, 1990

[30] Foreign Application Priority Data

Nov. 3, 1989 [GB] United Kingdom ............... 8924841

[51] Int. Cl.$^5$ .................. E21B 49/08; G01N 1/00
[52] U.S. Cl. ............................ 73/864.31; 73/155; 166/264
[58] Field of Search ............... 73/155, 864.63; 166/264

[56] References Cited

U.S. PATENT DOCUMENTS

| | | | |
|---|---|---|---|
| 2,657,576 | 11/1953 | Boykin | 73/155 |
| 2,862,561 | 12/1958 | Teubner | 73/864.63 |
| 3,055,764 | 9/1962 | Pryor et al. | 73/864.63 |
| 4,811,599 | 3/1989 | Johnson et al. | 73/155 |

FOREIGN PATENT DOCUMENTS

0221793' 5/1985 German Democratic Rep. ............... 166/264

Primary Examiner—Hezron E. Williams
Assistant Examiner—George Dombroske
Attorney, Agent, or Firm—Anthony Asquith & Co.

[57] ABSTRACT

The down-hole sampler comprises a reservoir, with screw-down type valves top and bottom. The valves are arranged with the axes of the screw threads vertical. The valve members are integral with the structure of the sampler, whereby even with the valves screwed open, the sampler and the valves remain structurally intact. The sampler has a very slim overall diameter (down to 6 mm) and yet the valves are easy to operate, and sturdy and reliable in operation. The sampler includes a surface-operated check-valve for admitting a water sample into the reservoir.

6 Claims, 2 Drawing Sheets

APPARATUS FOR COLLECTING SAMPLES FROM GROUND-HOLES

This invention relates to the collection of a sample of groundwater from a well or test bore.

In the field of groundwater sampling and analysis, it is becoming increasingly important to provide an accurate indication of the amount of volatile organic materials present in the water.

Volatile organics, or dissolved gases such as radon, pose special difficulties for the test engineer. When a sample of groundwater has been brought to the surface, and transported to the laboratory for analysis, the quantities and proportions of dissolved chemical pollutants, gases, solids in suspension, and the like, are expected to be the same in the sample, during analysis, as they were in the water in the hole. But the proportions and quantities of the volatile organics and dissolved gases are not so stable. The equilibrium proportions of the volatiles relative to the water depends upon the pressure of the water: so that if the pressure drops, sometimes the volatiles might start to come out of solution.

Conventional methods of bringing a groundwater sample to the surface have generally involved exposing the sample to the atmosphere; this was perfectly acceptable when the analysis was concerned only with detecting inorgainc chemical pollutants, but exposing the sample to the air is quite unacceptable when the analysis is concerned with volatile organic pollutants or dissolved gases.

In order for the results of an analysis to be trustworthy, for example in the case of a investigation into a contaminant spill, the engineer must be able to state to the tribunal that the sample was at no time exposed to the atmosphere, from the moment the sample was removed from its resident depth in the ground-hole until the moment it was injected into the chromatography machine, mass spectrometer, or other analysis apparatus.

First, it is useful for the engineer to be able to state that the sample has been at least contained in a sealed reservoir, so that no gases or volatiles can have escaped, and also so that the sample cannot have been tainted by picking up anything from the atmosphere. But it is even better if the engineer can state not only that the sample has been contained, but that the pressure of the sample has never been allowed to fall below the in-ground value. If the pressure on the sample has been maintained, the engineer may assert that the gaseous and the liquid phases of the sample are in the same state of homogeneous equilibrium in the water of the sample as in the water of the ground-hole. As stated, it is important to be able to demonstrate that false readings cannot have happened. Apart from the separation of the volatiles due to a drop in pressure, of course there are other potential sources of error that should be eliminated, and should be seen to be so. Thus, sampling apparatus should be so designed that the reservoir contains only water from the test depth (and not, for example, water picked up as the sample was being lowered to the test depth). Proposals have been made previously for apparatus which enables a sample to be collected in such a manner that the reservoir contains only water from the test depth and in which the contents of the reservoir can be contained and isolated in the reservoir right up to the moment of analysis. Examples are shown in U.S. Pat. No. 4,811,599 (JOHNSON, Mar. 89) and GB 2215704 (SOLINST, Sept. 89).

In the prior art, the apparatus incorporates a check valve which is located at the bottom of the reservoir. The reservoir is open to a (gaseous, e.g. nitrogen) pressure source, located at the surface and connected to the reservoir via a tube, which, when pressure is applied, serves to keep the check valve closed. Thus, the sampler may be lowered to the collection depth with the check valve closed.

Upon reaching the test depth, the pressure is released, which allows the check valve to open, and allows water to flow into the reservoir. The water rises up the reservoir and up the tube until the pressure in the reservoir equals the pressure in the ground hole at the sampling depth. The pressure is then re-applied, which allows the check valve to close, and the reservoir is brought out of the ground. The pressure remains applied to the reservoir during the period the reservoir is being raised. When out of the ground, the reservoir can be closed, and sealed, with the contents still under pressure, by the means as described for example in the JOHNSON and SOLINST patents.

The present invention uses the same procedure, wherein pressure is applied from the surface to control the action of a check valve, and wherein pressure is maintained on the reservoir until the reservoir has been isolated and sealed. The invention also shares with the prior art the feature that the sample inside the reservoir may be fed into the analysis machine while still under pressure, or at least still contained and isolated.

It is often not regarded as good enough for the sample to be merely contained: almost as important is that sample should be maintained at the same pressure it experienced at depth, in the hole. The maintenance of pressure is regarded as important for the following reasons.

If the sample is merely contained—if, for example, a small sample of (liquid) water is contained in a large container—then it cannot be ruled out that some of the volatile components or dissolved gases might separate out (i.e. might "bubble" out) of the liquid, and into the empty space within the container. Then, when the liquid is injected into the chromatography machine, some of its constituents are missing.

Whether this actually happens is not important: the issue is that it might happen, and therefore the results of the analysis cannot be trusted. It may be noted that volatile components are not lost instantly, and therefore a momentary loss of pressure may be disregarded; however, the chances are unacceptably high that the volatile components or dissolved gases will tend to separate out if the sample is stored for a prolonged period at a reduced pressure.

In many cases, though, the presence of the volatiles themselves can maintain the pressure within the reservoir at more or less the in-hole level. Thus, when the reservoir has been brought to the surface, and its contents are still under pressure, then it may be assumed that, after the reservoir is sealed, it is completely filled with liquid.

In the invention, the basic construction of, and manner of operating, the sampler correspond to that shown in the prior art. The invention differs as regards the construction of the valves. The invention is aimed at making the sampler compact (in the diametral sense), easy to operate, able to seal the reservoir in a reliably secure manner, flexible in application, and able to protect the sample against possible contamination.

One of the main attributes of the invention is that it permits the sampler to be very compact as to its diameter, so that only very narrow monitoring wells need be provided. In the prior art, the compromise between diametral compactness, robustness of construction, and reliability of operation has been less favourable than is the case in the invention.

GENERAL FEATURES OF THE INVENTION

In the invention, the reservoir sealing valves are of the screw-down type, in which a ball is forced onto a conical seating by the action of tightening a screw. Such screw-down ball valves are in widespread use in many different applications, and are characterized by the reliability with which they are regarded as leakproof.

In the invention, the screw-thread of the screw-down ball valve is disposed axially with respect to the sampler (i.e. with respect to the ground-hole).

It is this in-line arrangement of the screw thread of the valve which permits the sampler of the invention to be so compact, diametrally.

In the invention, the valve is a part of the structure of the sampler. Thus, even when the valve is open, the structural integrity of the sampler depends on the screw-thread connection. When the valve is open, the screw thread is loose, and, in the invention, the sampler has to be such that it can be lowered into, and raised out of, the ground-hole, with the valve screwed open. It is recognized in the invention that the required degree of structural integrity can be achieved in a non-tightened screw-thread, in the circumstances in which the sampler will be used.

In the invention, it is recognized that the screw thread preferably should be sealed, even when the screw thread is loose (in fact especially then) to prevent dirt entering the reservoir, and to prevent the sample from leaking out before the valves can be screwed closed.

Preferably, in the invention, it should be possible to open and close the screw-down valves by hand, while holding the sampler in the hands. It may be noted that the act of opening and closing the valves is carried out in the field, i.e. at the ground-hole test site. In this regard, it may be noted also that the components of the sampler, including the valves, should be robust enough for field use.

DETAILED DESCRIPTION OF PREFERRED EMBODIMENT

By way of further explanation of the invention, an exemplary embodiment of the invention will now be described with reference to the accompanying drawings, in which.

Figure 2:
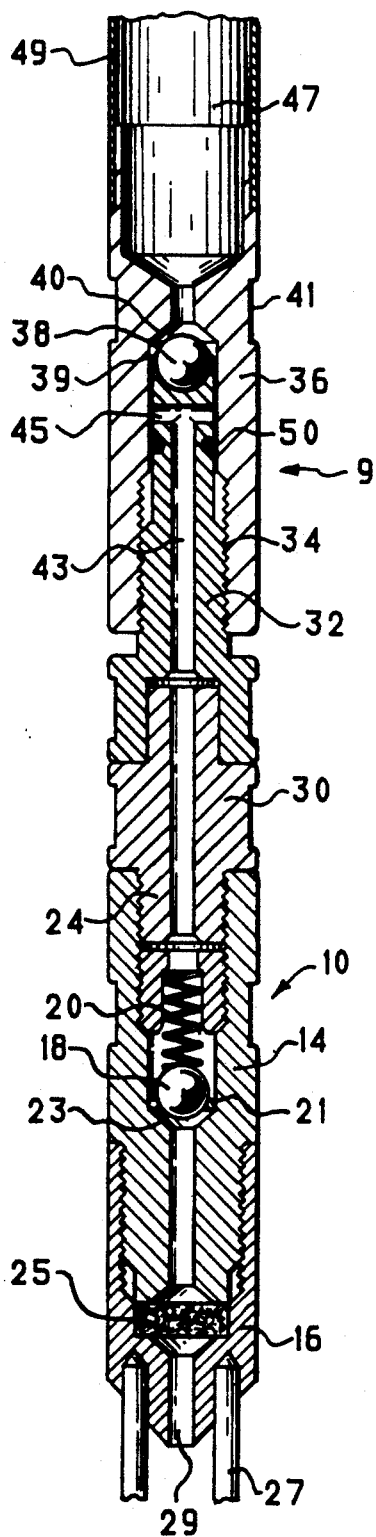
FIG. 2 is a close up of the bottom region of the sampling apparatus of FIG. 1.
Figure 1:
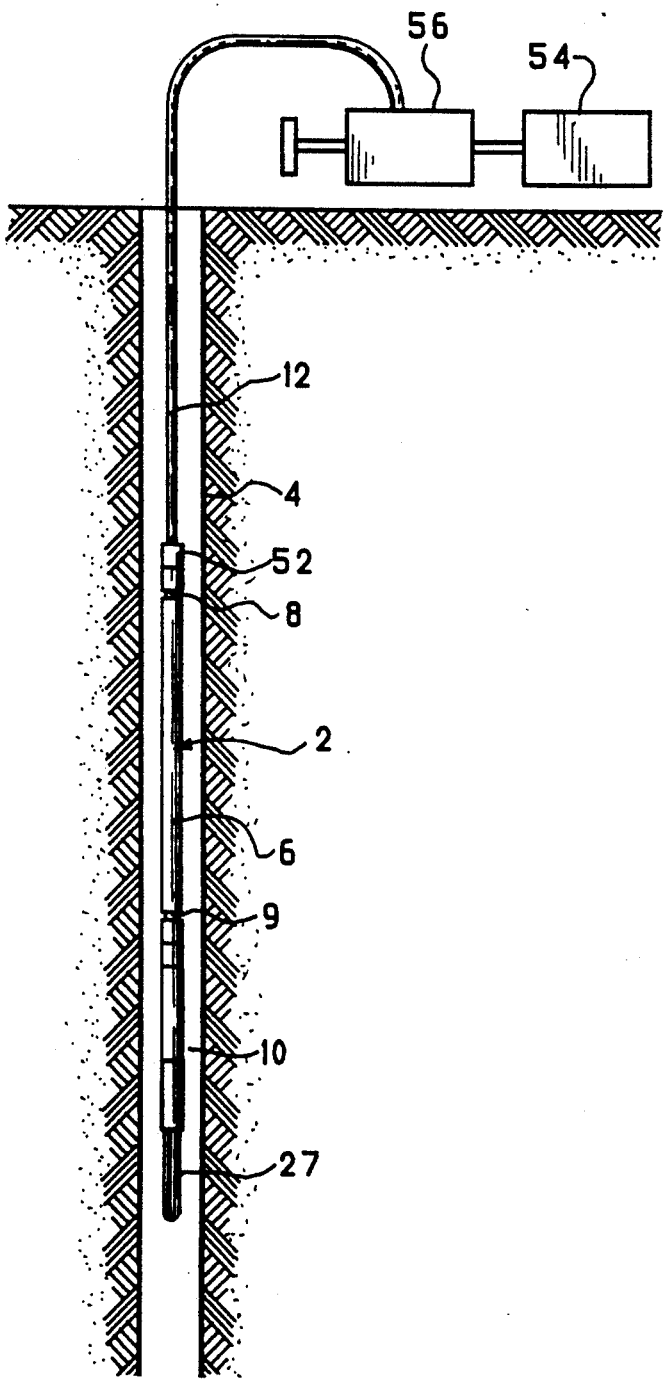
FIG. 1 is a section of a borehole, into which has been inserted a sampling apparatus which embodies the present invention.

The apparatus shown in the accompanying drawings and described below are examples which embody the invention. It should be noted that the scope of the invention is defined by the accompanying claims, and not necessarily by specific features of exemplary embodiments.

The apparatus includes a sampler 2, which is adapted to be lowered into, and raised out of, the hole in the centre of a liner 4. The liner 4 may be one of a bundle of liners inserted to different depths in a hole in the ground. The ground hole is prepared with an auger; the auger is of the hollow-stem type, and the bundle of liners, each of a different depth, is passed down the hollow stem. The auger is removed once the liners are in place.

After the liners are in place, the site may be left for several days, to allow the ground water conditions to stabilize.

The sampler is manipulated into the liner 4 either by hand or by a suitable hoist apparatus. The details of the manner of forming the hole, and of lowering and raising the sampler, are conventional and are not described.

The liner 4 is blanked off at its bottom end, and suitable slits are cut in the liner to allow water to enter but to keep particles of dirt out. Inevitably, however, there will be a build-up of fine slit in the bottom of the liner.

The sampler 2 includes a reservoir 6, which is provided with an upper screw-down valve 8 and a lower screw-down valve 9. The arrangement is that if these valves 8,9 are open, water may flow into and through the reservoir 6; if the valves 8,9 are closed, the hollow interior of the reservoir 6 becomes an enclosed sealed chamber of fixed volume.

The sampler also includes a pressure operated one-way check-valve 10, which is located below the lower screw-down valve 9.

The upper screw-down valve 8 is coupled to a length of tubing 12, made of suitable plastic material, by means of which the sampler 2 may be lowered and raised in the liner 4.

It is customary to arrange two communicating samplers in vertical tandem, i.e. one above the other, whereby both samplers are filled with water from the same depth, since it is customarily required that a back-up sample be available.

The one-way check valve 10 includes a body 14. A ball 18 is urged by a spring 20 against an O-ring 21, which resides in a valve seating 23. The spring is held in place by means of a screwed-in retainer 24. The spring serves to urge the ball normally into the valve-closed position, so that the ball closes reliably when pressure is applied.

Water entering the sampler, via the passageway below the ball 18, passes first through a filter 25. The filter 25 is a block of stainless steel micro-pore material, which is held in place between the body 14 and the end cap 16. An end cap 16 includes a guard 27, which protects the entry port 29 from direct contact with sediment etc that may be present at the bottom of the liner 4. The filter 25 serves to prevent dirt particles from entering the reservoir.

An adapter 30 connects the body 14 of the check valve 10 to the valve-insert 32 of the lower screw-down valve 9. The insert 32 is in screw-threaded connection, at 34, with a valve housing 36. A ball 38 is secured in the end of the insert 32 by swaging the cylindrical nose 39 of the insert inwards. The ball 38 is adapted to engage, and to seal against, a conical valve seating 40 formed in the housing 36.

When the valve-insert 32 is turned relative to the housing 36, the screw connection 34 drives the ball 38 towards or away from the seating 40. Thus the status of the valve 9, i.e. whether the valve is open or closed, may be controlled by twisting the insert relative to the housing. This twisting operation is carried out by the engineer, who sees to it that the valve 9 is open, by about one full turn of the thread at 34, before the sampler is lowered down the liner. The twisting may be done by hand, i.e. with the fingers, or a wrench may be applied to flats 41 which are provided for the purpose. If the ball is made of plastic material, a wrench should not be used because it would be too easy to damage the ball by over-tightening the thread.

The screw-down valve 9 should not be opened too widely, as there is a (remote) possibility that, during the operation of lowering the sampler, the sampler may be jarred in such a way as to shake the thread loose. Equally, the valve should be substantially open, so that the flow of water into and through the valve is not inhibited.

It may be noted that, when the valve 9 is open, the total physical and mechanical connection between those components of the sampler that lie above the valve, and the components that lie below the valve, is by means of the loose screw thread connection 34. The length of the treaded engagement, and the diameter and other dimensions of the thread, are designed with this requirement in mind.

The insert 32 includes a central passageway 43, which opens into a cross-drilling 45. When the valve 9 is open, water may flow from the cross drilling 45, around the nose 39 and ball 38, through the seating 40, and into the hollow interior 47 of a tube 49. The tube 49 is silver-soldered to the housing 36 of the valve.

An O-ring seal 50 serves to prevent the sample water leaking out, and outside water leaking in, whereby the engineer may be certain that all the water contained within the reservoir 6 has entered via the port 29. The O-ring 50 also provides some frictional resistance against unwanted unscrewing of the insert 32 relative to the housing 36.

The upper screw-down valve 8 is identical to the valve 9, except that the valve 8 is inverted. The valve 8 also is screwed open before the sampler is to be lowered down the liner.

An adapter 52 is used to couple the upper valve 8 to the plastic tubing 12.

Above ground, the plastic tubing is connected to a pressure source 54, which includes a control valve 56. The fluid used in the pressure source may be air, but generally it is preferred that a more inert gas be used, such as nitrogen.

In use, to obtain a sample, the engineer first opens both screw-down valves 8,9 by about one turn. Next, he opens the control valve 56, to pressurize the interior of the reservoir. The pressurized fluid passes through the screw-down valves 8,9 and acts upon the check valve 10. The pressure acts to close the ball 18. The engineer takes care to supply sufficient pressure to keep the valve 10 closed against whatever pressure is present at the test depth within the liner 4.

With the valve 10 held closed by the prssure, the sampler is lowered into the liner. When the sampler is at the test depth, the engineer releases the pressure from the control valve 56. The valve 10 now opens, and water from the hole enters the port 29, fills the chamber 47, and passes up into the plastic tubing 12. The water will rise up the tubing 12 until it reaches the natural level of the water in the liner; all the water inside the reservoir is water from the test depth, i.e. water that has flowed in through the port 29.

After a short period, the flow of water will have stopped. At that point, the engineer re-applies the pressure, so that the valve 10 closes once more. He pulls the sampler out of the liner, with the pressure still maintained, and therefore the valve 10 still closed.

The engineer should set the pressure so that the water sealed in the reservoir is at the pressure it was at when in the ground. It may be noted that it is the head of water above the sampling point which gives rise to the in-ground pressure. If the in-ground pressure is say 20 psi, then it is required that the sample be sealed into the reservoir also at 20 psi. However, if the pressure of 20 psi is applied at the surface, the reservoir being still in the ground at that point, the pressure in the reservoir will actually rise to 40 psi. The reservoir pressure only drops to 20 psi as the tubing and reservoir is withdrawn from the liner and laid out horizontally. If this increase in pressure is felt to be unacceptable, it is possible for the engineer to manipulate the pressure so that the reservoir pressure remains constant at 20 psi.

When the sampler emerges from the liner 4, the engineer screws both of the screw-down valves 8,9 closed, thus trapping a sample of the water inside the chamber 47 of the reservoir 6. With the valves 8,9 closed, he may now unscrew the adapter 30 from the valve 9 and lay the check-valve 10 aside, and, after releasing the pressure, he may unscrew the adapter 52 from the valve 8. The engineer should take care to ensure that the valves 8,9 are screwed closed before releasing the pressure, and before attempting to unscrew any of the connections.

Assuming he wishes to continue obtaining further samples, after disconnecting the reservoir the engineer blows out the water remaining in the plastic tubing 12, and carries out whatever cleansing and decontaminating is required; he assembles a fresh reservoir and screws the adapters 30,52 thereto. He then repeats the procedures described above.

Figure 3:
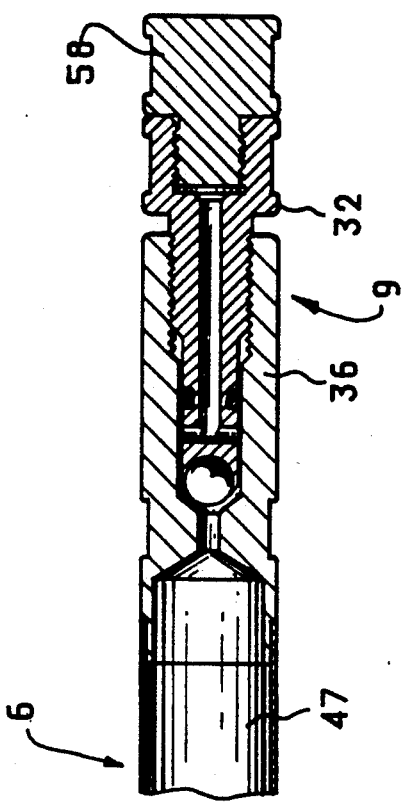
FIG. 3 is a cross-section of a reservoir of the apparatus of FIG. 1, the reservoir being shown in the transit and storage condition.
Figure 3:
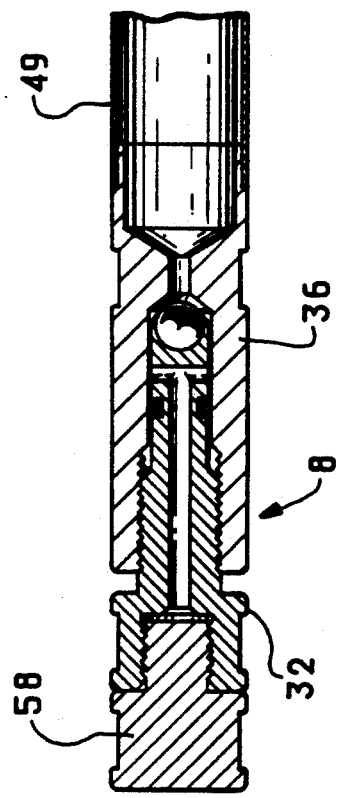

The reservoir 6, containing the sample, is to be transported to the laboratory. Protective bungs 58 are inserted into the open ends of the valves 8,9, where the adapters 30,52 came from, to protect the reservoir during transit and storage (FIG. 3).

At the laboratory, the sample, or a portion of the sample, is to be extracted from the reservoir and passed into a gas chromatography machine.

Figure 4:
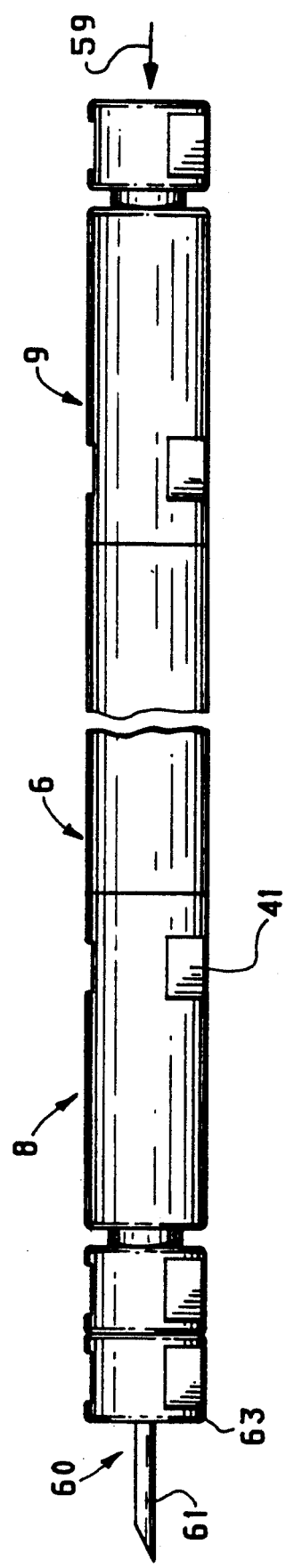
FIG. 4 is an elevation of the reservoir of FIG. 3, which has been arranged for transfer of the contents of the reservoir to a chromatography analyser.

The bungs 58 are removed from the ends of the reservoir, and set aside. With the valves 8,9 still closed, a source 59 of pressurized nitrogen is coupled to one end of the reservoir, and a device 60 for tranferring the sample to an analysis machine is coupled to the other end. The device 60 includes a syringe needle 61, which is fixed to an adapter 63 (FIG. 4).

When these couplings are made, the valves 8,9 may be opened to admit pressure into the chamber 47. A small quantity of the sample is allowed to escape through the needle 61, so as to ensure that there are no air bubbles in the needle. The needle is then inserted into the receiving membrane of the chromatography machine, and the pressure at the other end of the reservoir serves to inject the water into the machine.

Generally, only a small portion of the sample is needed for the analysis, and it is desirable that the rest of the sample may be retained. After the portion has been removed, the chamber 47 is now no longer filled with liquid, i.e. there is a space within the reservoir; however, the sample may be kept homogeneous, i.e. the volatiles may be prevented from bubbling out of the sample water, providing the reduced volume sample is maintained under pressure. This can be done by closing the valves 8,9 while the pressure is still on.

Alternatively, a syringe body may be used in place of the needle 61, and the sample is passed into the syringe body. The syringe may then be removed from the reservoir, prior to injecting the sample into the analysis machine. With care in the operation, and the right equipment, sample pressure can be maintained right up to injection.

It is recognised that the design of the sampler, as described, permits the pressure to be maintained on the sample, even under the conditions as noted.

When the valves 8,9 are closed the chamber 47 may be regarded as being of a constant volume. However, it can happen that the chamber might expand due to temperature changes during transit and storage, thus relieving the pressure of the test liquid inside, and perhaps causing the volatile components to separate out of solution. However, such a change in volume of the chamber is likely to be very small: if the volatiles are present in large quantities, then the pressure will be maintained, since the trapped gases will simply expand to fill the gaps, with substantially no drop in pressure, and the sample remains homogeneous; if the quantity of volatile components is too small to maintain the pressure, then generally the quantity is too small to have any significance.

The material of the components should be such as to eliminate any possibility of the sample becoming contaminated. The metal components are all of stainless steel. The ball 38 may alternatively be of inert plastic, such as Teflon (trademark). The O-rings are of Viton (trademark).

When the sampler is being lowered down the liner, it is full of gas, preferably nitrogen. The sampler will therefore tend to have buoyancy as it enters the water. The engineer must take care in the design of the sampler that it has sufficient weight to overcome the buoyancy.

As mentioned, the plastic tubing 12 is the means by which the sampler is pulled out of the liner 4. The sampler is lowered into position down the liner 4, and therefore, the tubing 12 must be strong enough to support the act of pulling the sampler out from the liner. In addition, the screw-thread connection 34, even when not tightened, must be capable of supporting the pull-out force.

The sampler as described is very compact as to its diameter, and the outer shape of the sampler is smooth and without protrusions. The sampler is thus able to fit easily in the smallest of sampling wells, liners, open tube piezometers, and the like. These advantages arise predominantly because the screw-threads of the screw-down valves are disposed axially, i.e. along the length of the sampler. The axially disposed valves are a part of the structure of the sampler, in that the various components of the sampler are held together by the same screw-threads as are used to open and close the valves. This arrangement gives compactness, and does not, as might have been expected, pose any substantial limitation on the manner of use of the sampler.

The same design of sampler of course can be used in cases where there is little restriction on the size of the sampler. If desired, the reservoir may be of larger diameter than the screw-down valves: the valves as described are however so easy for the technician to operate both in the field and in the analysis laboratory, so reliable as to their open or closed status, and so robust, as to be preferred even when diametral compactness is not of the essence. It is contemplated that the same valves and other components be used in conjunction with a number of different diameters of reservoir, for wells of different sizes.

On the other hand, it is quite possible, with careful attention to detailed design, to make a sampler which is robust and reliable enough for field operation, and which has an outside diameter of no more than 6 mm, using the principles of the invention. Below that size, the O-rings become too tiny to seal reliably,

I claim:

1. Sampling apparatus, for extracting a sample of groundwater from a borehole, wherein:
   the apparatus includes a sampler;
   the apparatus includes a suspension line, which extends between the sampler and the ground surface, and which is suitable for physically raising and lowering the sampler into and out of the borehole;
   the sampler includes a reservoir member;
   the reservoir member has the shape of a long, thin cylinder, the axis of the cylinder being vertical when the sampler is in the borehole;
   the reservoir member has a hollow interior, and is provided with at least an upper fluid-passing port;
   the upper port is in operative association with an upper screw-down valve;
   the upper screw-down valve includes a valve seating member and a valve insert member;
   the upper screw-down valve includes a screw-thread connection between the valve seating member and the valve insert member, whereby the members can be mutually screwed between a closed condition, in which fluid is prevented from passing through the port, and an open condition;
   the sampler includes a first suspension connection between the suspension line and one of the valve members, by means of which the said one valve member is directly physically suspended from the suspension line;
   the sampler includes a second suspension connection between the other of the valve members and the reservoir, by means of which the reservoir is directly physically suspended from the said other valve member:
   the axis of the said screw-thread connection between the valve members is vertical when the sampler is in the borehole;
   the arrangement of the screw thread connection between the valve members is such that the screw-thread connection comprises a means for directly physically suspending the one valve member from the other valve member, even when the screw-thread connection is in the fluid-passing, or valve-open, condition.

2. Assembly of claim 1, wherein
   the reservoir member is provided with a lower fluid-passing port;
   the lower port is in operative association with a lower screw-down valve;
   the lower screw-down valve includes a valve seating member and a valve insert member;
   the lower screw-down valve includes a screw-thread connection between the valve seating member and the valve insert member, whereby the members can be mutually screwed between a closed condition, in which fluid is prevented from passing through the lower port, and an open condition;

the sampler includes a fluid-pressure-operable check-valve, which is operable between a closed condition, in which fluid is prevented from passing through the lower port, and an open condition;

the sampler includes a first lower suspension connection between the reservoir and one of the lower valve members, by means of which the said one lower valve member is directly physically suspended from the reservoir;

the sampler includes a second lower suspension connection between the other of the valve members and the check-valve, by means of which the check-valve is directly physically suspended from the said other lower valve member;

the axis of the said screw-thread connection between the lower valve members is vertical when the sampler is in the borehole;

the arrangement of the screw thread connection between the lower valve members is such that the screw-thread connection comprises a means for directly physically suspending the, one lower valve member from the other lower valve member, even when the screw-thread connection is in the fluid-passing, or valve-open, condition.

3. Assembly of claim 2, wherein the apparatus includes a fluid line, for transmitting fluids between the groundsurface and the sampler, and wherein the arrangement of the sampler is such that that a fluid-passing connection is established, when the upper and lower valves are open, from the fluid line, through the upper port, through the reservoir, through the lower port, and to the check valve.

4. Assembly of claim 2, wherein:

the said means for physically connecting one of the upper valve members to the suspension line includes a means for detching the said one of the members therefrom, when the sampler is out of the borehole;

the said means for physically connecting one of the lower valve members to the check valve includes a means for detching the said one of the members therefrom, when the sampler is out of the borehole;

whereby, when the upper and lower valves are in the closed condition, and when the said one of the upper valve members is detached from the suspension line, and when the said one of the lower valve members is detached from the check valve, the interior of the reservoir remains sealed between the upper and lower valves.

5. Assembly of claim 1, wherein:

the valve insert member and the valve seating member are both so formed as to define respective central fluid-passing openings, in communication with the said port;

the screw-down valve includes a ball, which is larger in diameter than the cross-section of the said openings;

the ball is positioned between the members, the arrangement of the valve being such that, when the valve is closed, the ball is effective to close off the said openings.

6. Assembly of claim 3, wherein:

the upper and lower valves include respective sealing means;

the sealing means are effective, when the valves are in the open condition, to prevent leakage of fluid through the screw thread connections.

* * * * *